United States Patent [19]

Anami

[11] Patent Number: 5,380,486
[45] Date of Patent: Jan. 10, 1995

[54] APPARATUS FOR TAKING LIQUID CONTENT FOR USE IN ANALYSIS OUT OF CONTAINER

[75] Inventor: Takayuki Anami, Iruma, Japan

[73] Assignee: Olympus Optical Co., Ltd., Tokyo, Japan

[21] Appl. No.: 868,878

[22] Filed: Apr. 16, 1992

[30] Foreign Application Priority Data

Apr. 19, 1991 [JP] Japan .................. 3-113786
Apr. 19, 1991 [JP] Japan .................. 3-113787

[51] Int. Cl.$^6$ ............... G01N 33/48; B01L 3/14; B67B 7/16
[52] U.S. Cl. .................. 422/63; 422/100; 422/81; 73/863.01; 73/863.83; 73/863.85; 73/864.21; 73/864.22; 73/864.24; 53/381.4
[58] Field of Search ............ 53/381.4, 492; 73/863.01, 863.83, 863.84, 863.85, 864.21, 864.22, 864.24; 422/63, 64, 65, 99, 100, 81

[56] References Cited

U.S. PATENT DOCUMENTS

| | | | |
|---|---|---|---|
| 3,178,266 | 4/1965 | Anthon | 422/64 |
| 3,872,730 | 3/1975 | Ringrod et al. | 73/421 B |
| 3,894,438 | 7/1975 | Ginsberg | 73/423 A |
| 3,901,656 | 8/1975 | Durkos et al. | 23/230 B |
| 3,994,687 | 11/1976 | Engelbrecht | 73/864.22 |
| 4,217,798 | 8/1980 | McCarthy et al. | 81/3.2 |
| 4,475,411 | 10/1984 | Wellerfors | 73/864.24 |
| 4,478,095 | 10/1984 | Bradley et al. | 73/864.21 |
| 4,558,603 | 12/1985 | Chlosta et al. | 73/864.21 |
| 4,803,050 | 2/1989 | Mack | 422/65 |
| 4,811,611 | 3/1989 | Uffenheimer | 73/864.22 |
| 4,815,325 | 3/1989 | Averette | 73/864.21 |
| 4,841,818 | 6/1989 | Plapp et al. | 81/3.08 |
| 4,861,553 | 8/1989 | Mawhirt et al. | 422/65 |
| 4,928,539 | 5/1990 | Champseix et al. | 73/864.24 |
| 4,938,929 | 7/1990 | Bost | 422/100 |
| 4,951,512 | 8/1990 | Mazza et al. | 73/861.23 |
| 4,962,041 | 10/1990 | Roginski | 436/150 |
| 4,994,240 | 2/1991 | Hayashi | 422/63 |
| 5,013,529 | 5/1991 | Itoh | 422/100 |
| 5,130,254 | 7/1992 | Collier et al. | 436/54 |
| 5,151,184 | 9/1992 | Ferkany | 210/514 |
| 5,201,794 | 4/1993 | Kasai et al. | 73/863.01 |
| 5,216,926 | 6/1993 | Lipscomb | 73/863.01 X |

FOREIGN PATENT DOCUMENTS

| | | |
|---|---|---|
| 0452892 | 10/1991 | European Pat. Off. . |
| 257819 | 6/1988 | German Dem. Rep. . |
| 2312010 | 9/1973 | Germany . |
| 2508704 | 8/1976 | Germany . |
| 2640036 | 3/1978 | Germany . |
| 2907558 | 8/1980 | Germany . |
| 3614954 | 11/1987 | Germany . |
| 403526 | 11/1965 | Switzerland . |

Primary Examiner—Donald E. Czaja
Assistant Examiner—Milton I. Cano
Attorney, Agent, or Firm—Stevens, Davis, Miller & Mosher

[57] ABSTRACT

An apparatus for taking a sample blood collected in a vacuum type blood collection tube having a main tube and a cap hermetically secured to an opening of the main tube, including a suction nozzle which is inserted into the main tube through the cap and an air supply nozzle which is also inserted into the main tube through the cap. During the sample blood is sucked into the suction nozzle, an air is supplied into the main tube through the air supply tube such that a pressure inside the main tube is kept substantially at the atmospheric pressure. The sample blood may be sucked, while the main tube is moved substantially up side down. In case of removing the cap by a cap removing mechanism, the air supply nozzle is inserted into the main tube through the cap and the pressure inside the main tube is increased to the atmospheric pressure or a positive pressure. A given amount of the blood sample can be taken out of the tube without being affected by the pressure inside the tube.

5 Claims, 9 Drawing Sheets

FIG_1
PRIOR ART
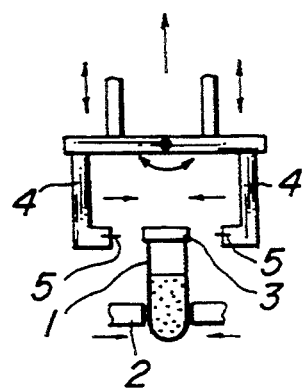

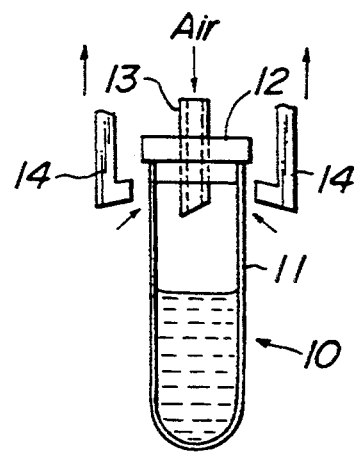

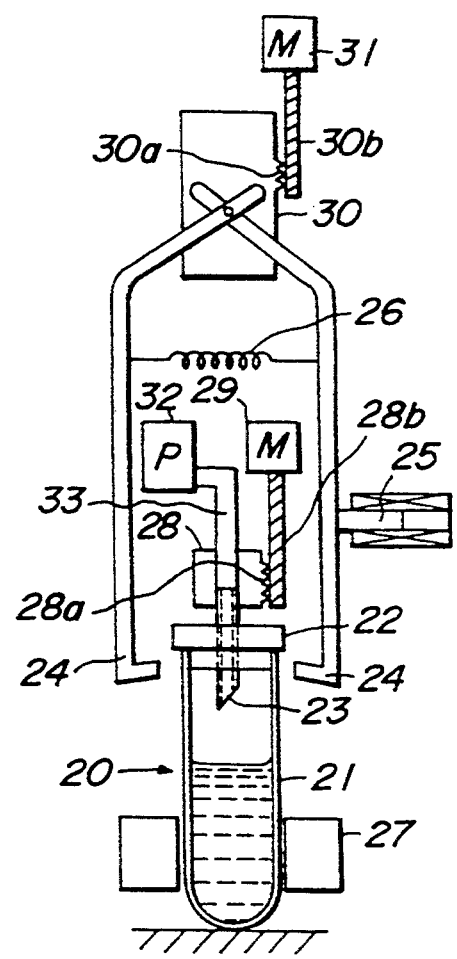
FIG_4

FIG_5
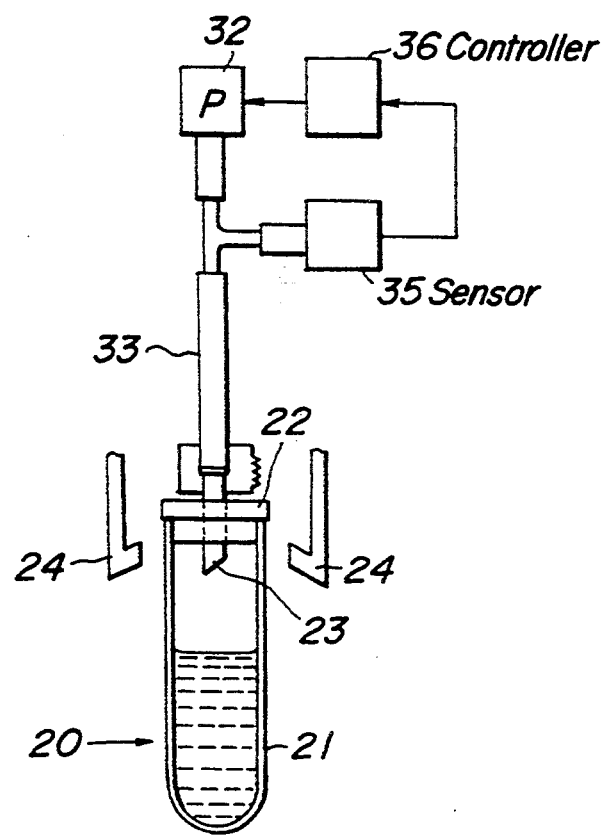
FIG_6
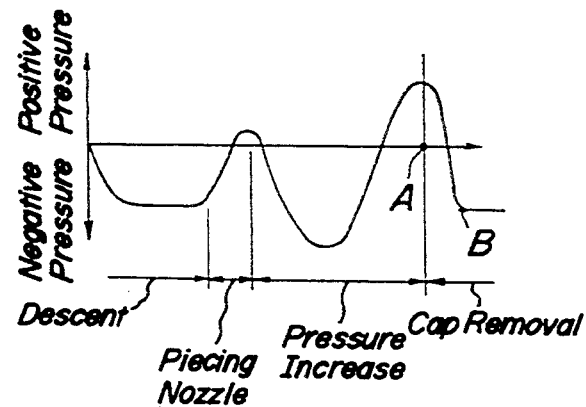

FIG_7
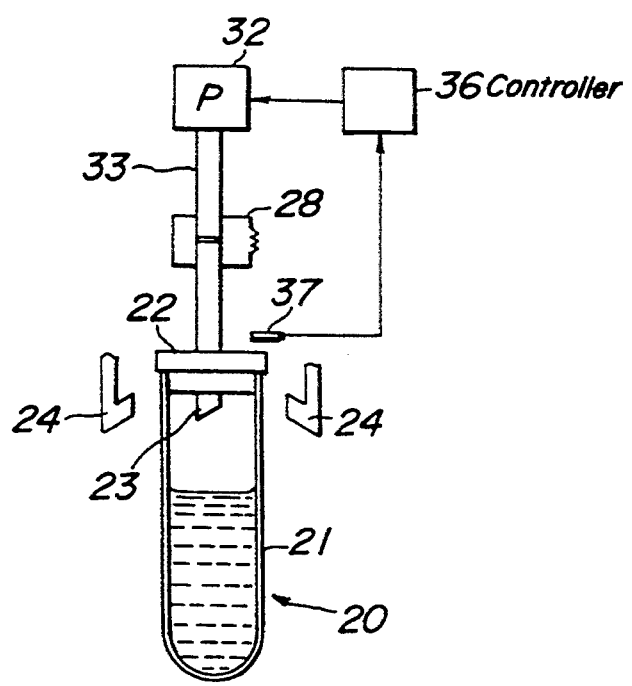

FIG_8
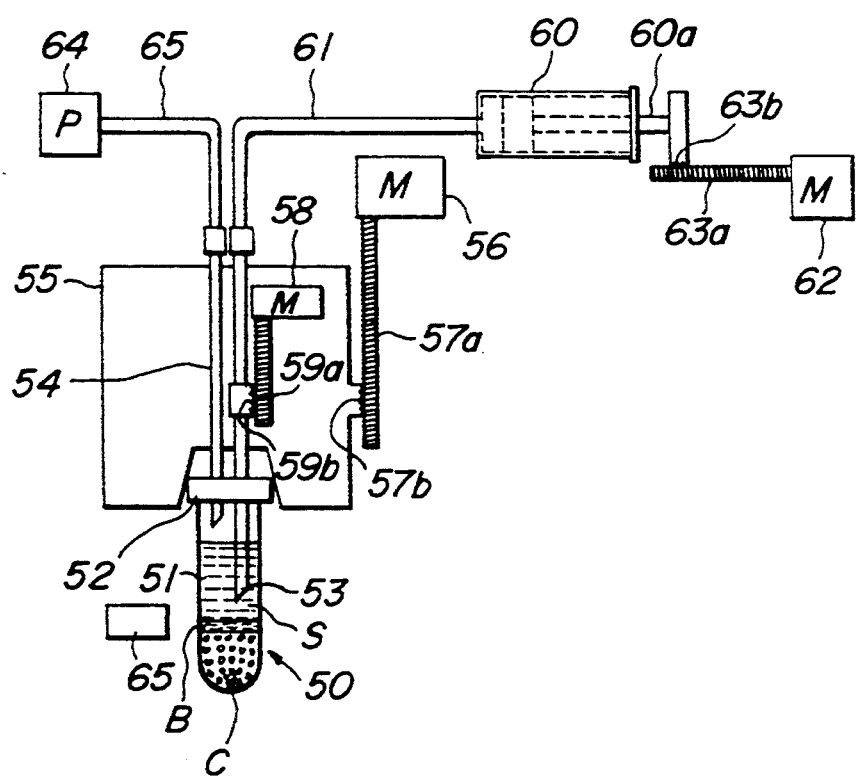

FIG_9
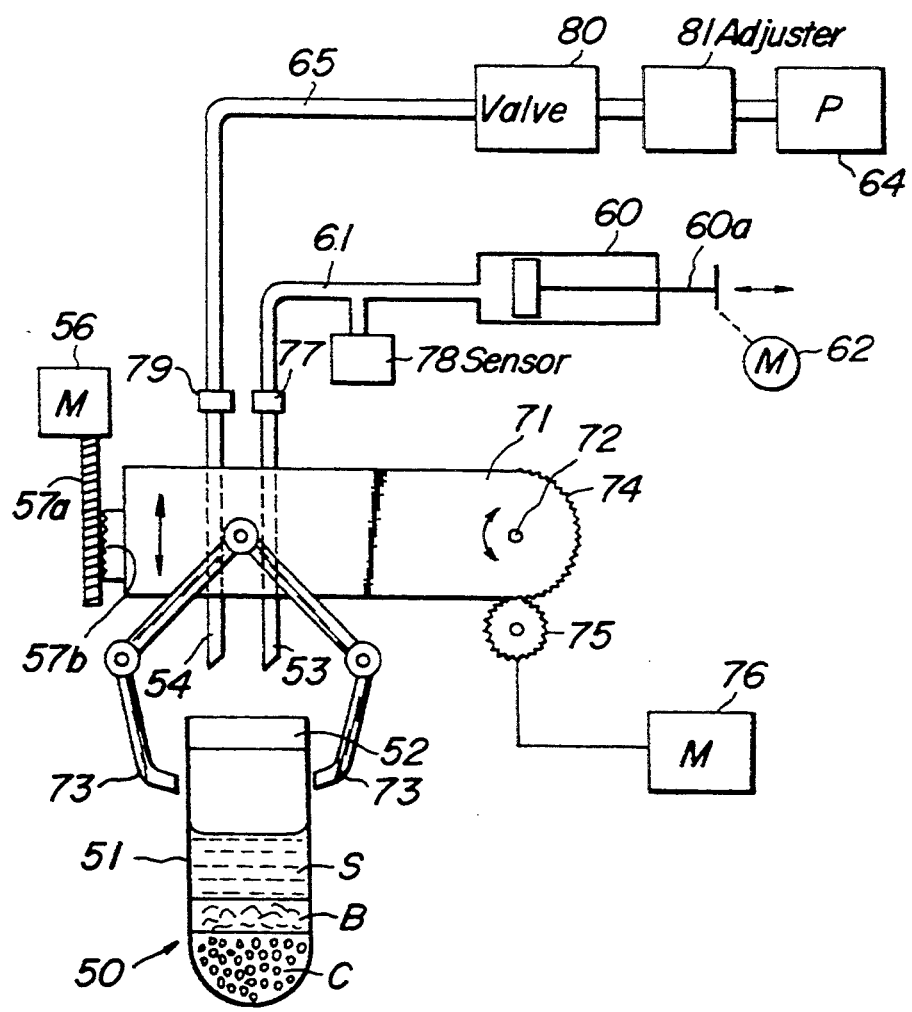

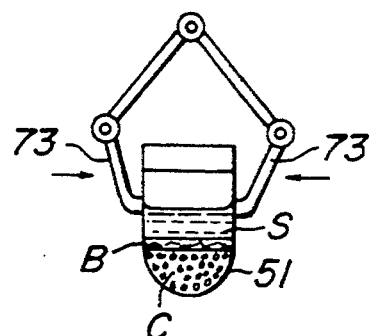
FIG_10A
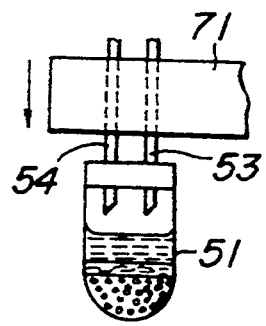
FIG_10B
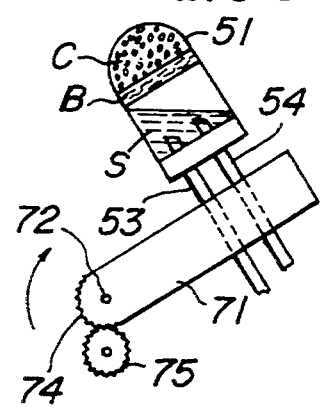
FIG_10C
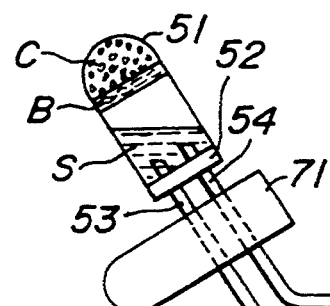
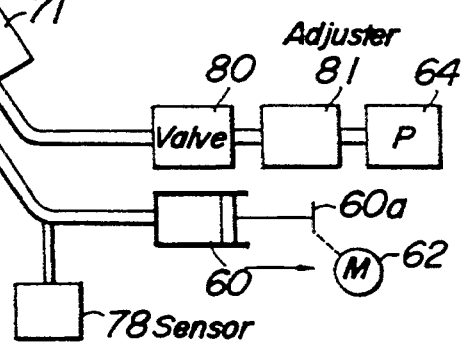
FIG_10D

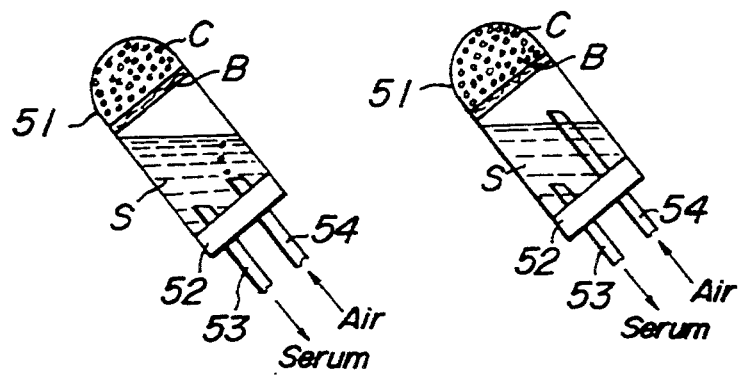

APPARATUS FOR TAKING LIQUID CONTENT FOR USE IN ANALYSIS OUT OF CONTAINER

BACKGROUND OF THE INVENTION

1. Field of the Invention

The present invention relates to an apparatus for taking a liquid content for use in analysis out of a container including a container main body having an opening and a cap secured hermetically to said opening to keep an inside of the container main body at a reduced or negative pressure.

2. Description of the Related Art Statement

In a chemical or biological analyzing system, a liquid content such as various kinds of samples derived from patients and reagents are usually contained in a container comprising a container main body having an opening and a cap hermetically is secured to the opening to keep the inside of the container main body. In order to store such a liquid content reliably, the liquid content is sometimes dried and dried substances are contained in the container. Upon usage, a solvent is added to form a solution and a given amount of the solution is taken out of the container. Apparatuses for taking a liquid content out of Such a container may be roughly classified into the following two types. In a first type, at first the cap is removed from the container main body, and then the liquid content is taken out of the container by inserting the suction nozzle into the container main body via the opening. In a second type of the apparatus, a suction nozzle having a tip in the form of a needle is inserted into the container main body by piercing the needle through the cap made of rubber and the liquid content is sucked into the suction nozzle.

In a blood analyzing system, a sample blood has to be taken out of a patient into a blood collection tube having a rubber cap. When the sample blood is collected from the patient, use is generally made of a vacuum type blood collection tube. In this type of blood collection tube, the inside of the tube is kept at a negative pressure and a sample blood is sucked into the tube effectively. After the sample blood has been sucked into the tube, the inside of the tube is still maintained at a negative pressure. Therefore, when the rubber cap is removed from the blood collection tube in order to take the sample blood out of the blood collection tube, the pressure inside the tube is abruptly increased from the negative pressure to the atmospheric pressure, so that the sample blood might be spread or overflowed from the tube. Then, an amount of the blood sample remained in the tube becomes small and a given amount of the sample blood could not be taken out. In this connection, it should be noted that nowadays test items to be analyzed for the sample blood has become larger, so that the collected blood sample has to used efficiently. Thus, when a part of the collected blood sample is overflowed from the blood collection tube, all the test items to be denoted for the sample blood could be no more performed. Moreover, since the pressure inside the tube varies during the operation for removing the rubber cap from the tube, control of a force for performing a punctual removal of the rubber cap in a determined time becomes very complex.

When the blood sample is taken out of the blood collection tube without removing the rubber cap, the suction nozzle having a needle secured to its distal end is inserted into the tube through the rubber cap such that the tip of the needle is immersed into the sample blood. After a given amount of the blood sample has been sucked into the suction nozzle, when the needle is removed out of the tube, an air is sucked into the needle, because the inside of the blood collection tube is maintained at the negative pressure. When the air is sucked into the needle and often makes undesired bubbles in the blood, an amount of the blood sample which is delivered from suction nozzle into a reaction vessel becomes smaller than a desired amount and the accuracy of the analysis is affected. Further, when the blood sample is sucked into the suction nozzle, the pressure inside the blood collection tube is reduced, and thus the control of the suction force for maintaining the accuracy of suction constantly becomes complicated.

When a serum of a sample blood is taken out of the vacuum type blood collection tube, the blood collection tube having the sample blood sucked therein is first set into a centrifugal apparatus and a serum and blood cells of the sample blood are separated from each other. Usually a separating agent mainly consisting of silicon is added to the blood sample. That is to say, the blood cells are collected into a lower portion of the tube as a clot and the serum is existent on the clot of blood cells. In order to take a given amount of the serum sample out of the tube, a suction nozzle is inserted into the tube through the rubber cap such that a tip of the serum sample sucking nozzle is immersed into the serum. However, a position of the tip of the suction nozzle in the serum is rather critical. When the suction nozzle is immersed into the serum deeply, undesired blood cells and separating agent might be sucked into the suction nozzle. Further the sucked blood cells and separation agent might clog the suction nozzle. On the contrary, when the suction nozzle is not sufficiently immersed into the serum, an amount of the sucked serum becomes smaller than a required amount. Moreover, an air might be introduced into the suction nozzle. Therefore, the suction nozzle has to be immersed into the serum such that its tip comes closer to a boundary between the clot and the serum. However, the position of the boundary between the clot and the serum varies for respective blood samples, so that it is necessary to detect the boundary. To this end, an assembly of a light source for emitting light and a photodetector for receiving the light emitted from the light source and transmitted through the blood collection tube is moved along a longitudinal axis of the tube. There is further proposed to use a sensor for detecting the position of the boundary by using light reflected by the boundary. However, usually on an outer surface of the blood collection tube there are provided a label on which patient number, edification number, patient name and so on are recorded and a bar code label. Sizes and positions of these labels on the tube differ widely from tube to tube. In some cases, a label is adhered around an entire surface of the tube. Therefore, it is very difficult to detect reliably the position of the boundary between the clot and the serum.

In order to detect the position of the boundary, there has been further proposed to measure an electrostatic capacitance or an electric resistance between electrodes which are secured to the tip of the suction nozzle and are immersed into the blood sample. However, such an electrical detection could not be performed reliably.

FIG. 1 shows a known apparatus for removing a rubber cap from an opening of a vacuum type blood collection tube. The apparatus comprises holding arms 2 for holding a vacuum type blood collecting tube 1 having an upper opening which is closed by a rubber cap 3 in a hermetical manner. The apparatus further comprises cap removing arms 4 which are arranged movably in a horizontal direction as well as in the vertical direction. On distal ends of the cap removing arms 4 there are secured pins 5 directing inwardly. After the tube 1 is held by the holding arms 2, the cap removing arms 4 are moved horizontally to come closer to each other and the pins 5 are penetrated into the rubber cap 3. Then, the cap removing arms 4 are moved upward to remove the rubber cap 3 from the tube opening. However, as stated above, the inside of the tube 1 is kept at the negative pressure, it is rather difficult to remove the rubber cap 3 only by moving the removing arms 4 upward. Therefore, an assembly of the cap removing arms 4 is arranged to be swingable about an axis which extends vertically to a plane of the drawing of FIG. 1 by means of any suitable swinging mechanism. When the cap removing arms 4 are swung, the rubber cap 3 is deformed to form a thin space between the cap and the tube so that an air is introduced into the tube 1 and the pressure inside the tube is gradually increased. In this manner, the rubber cap 3 can be removed from the blood collection tube 1.

In the known rubber cap removing apparatus shown in FIG. 1, it is necessary to swig the assembly of the cap removing arms 4, and this requires a very complicated swinging mechanism. Further when the tube 1 is made of glass, the tube is liable to be broken by the swinging movement.

Further, in the known apparatus, the pins 5 are inserted into the rubber cap 3, so that this apparatus could not be applied to other tubes which is made of other material or which is formed in different shapes.

In the chemical or biological analyzing system, the hermetically sealed container is generally vacuumed in order to avoid the evaporation of liquid substances, the oxidation of liquid or dried solid substances and the moisture absorption of dried substances. The dried substances are forming the powders by removing water and are stored in the container. When such dried substances are used, suitable solvent is supplied into the container to form a solution. Then a given amount of the solution is taken out of the container by either one of the above explained two methods. Such dried substances are enzymes, antigens and antibodies.

Further, the pressure inside the container may be reduced by providing the cap under the reduced pressure or by keeping the container at a low temperature after the cap is provided in the atmospheric pressure. In order to keep the reduced pressure reliably, a sealing member may be provided or the cap may be screwed into the opening of the container main body.

The container main body may be formed in any desired shape and the size of the opening has be sufficiently wide for introducing the suction nozzle into the container main body through the opening. The container main body may be made of any desired material which has a substantially hermetic property in accordance with chemical and physical properties, environments under which the container is kept and the frequency of usages. When the liquid content is taken out of the container after the cap has been removed, the cap may be made of any desired material which has a substantially hermetic property. However, when the liquid content is taken by piercing the suction nozzle through the cap, the cap has to be made of material which has a substantially hermetic property and which affords the piercing of the suction nozzle. Usually the cap is made of natural or synthetic rubbers. In case of taking liquid contents from these containers, the above mentioned problems would equally occur.

SUMMARY OF THE INVENTION

The present invention has for its object to provide a novel and useful apparatus for taking a liquid content for use in analysis from a container which includes a container main body having an opening and a cap which is hermetically secured to said opening to keep an inside of the container main body at a reduced pressure, in which a desired amount of the liquid content can be taken precisely without being influenced by the reduced pressure of the inside of the container main body.

It is another object of the invention to provide an apparatus for taking a liquid content for use in analysis from a container which includes a container main body having an opening and a cap which is hermetically secured to said opening to keep an inside of the container main body at a reduced pressure, in which the cap can be removed from the opening of the container main body easily so as to perform a constantly punctual operation of taking a liquid content out of a container without causing a rapid change in the pressure inside the container main body.

It is still another object of the invention to provide an apparatus for taking a liquid content for use in analysis from a container which includes a container main body having an opening and a cap which is hermetically secured to said opening to keep an inside of the container main body at a reduced pressure, in which a given amount of the liquid content can be taken out of the container by means of a suction nozzle without being affected by the pressure change.

According to a first aspect of the invention, an apparatus for taking a liquid content for use in analysis out of a container including a container main body having an opening and a cap which is hermetically secured to said opening to keep an inside of the container main body at a reduced pressure, comprises;

liquid content taking means including means for removing said cap from the opening of the container main body or a suction nozzle which is inserted into the container main body through said cap; and air supplying means for supplying an air into the container main body through said cap; whereby a pressure inside the container main body is controlled by supplying the air into the container main body while the cap is removed from the container main body or the liquid content is sucked into the suction nozzle.

According to the invention, when the cap is removed from the container main body, the air is supplied into the container main body such that the pressure inside the container main body is increased to the atmospheric pressure. Therefore, the cap can be easily removed, and any complicated swinging mechanism is not required. Further, when the pressure inside the container main body is increased up to a positive pressure, there is produced a force for pushing the cap upward. Then, the cap can be removed much more easily. In this case, when the air supply to the container main body is controlled such that when the cap is just removed, the pressure becomes the atmospheric pressure. Then, the liquid content contained in the container main body is not overflowed when the cap is removed from the container main body.

Further, in case of sucking the liquid content from the container main body by inserting the suction nozzle into the container main body via the cap, the air is gradually supplied into the container main body such that the pressure inside the container main body is not reduced, and thus the control for the suction force becomes simple and the air is not introduced into the suction nozzle when the suction nozzle is removed out of the container main body. In this manner, according to the invention, a given amount of the liquid content can be accurately taken out of the container.

According to the invention, said air supplying means comprises an air supply nozzle in the form of a needle which can be easily penetrated into the rubber cap. When this air supply nozzle is opened to the atmosphere, when the air supply nozzle is inserted into the container main body through the cap, the reduced pressure inside the container main body is increased to the atmospheric pressure. Further the air supply nozzle may be connected to an air supply pump such as an air compressor. Then, the introduction of the air into the container main body can be controlled such that the pressure inside the container main body is gradually increased.

In another preferable embodiment of the present invention, said air supplying means includes a means for detecting the pressure inside the container main body and a means for controlling the operation of the air supplying means in accordance with the detected pressure inside the container main body such that the pressure inside the container main body is kept substantially at the atmospheric pressure.

In this embodiment, the pressure inside the container main body is kept always at the atmospheric pressure, the removal of the cap from the container main body does not cause any undesired overflow of the liquid content from the container main body or the suction of the liquid content does not produce any undesired introduction of the air into the suction nozzle.

According to a second aspect of the present invention, an apparatus for taking a liquid content for use in analysis out of a container including a container main body having an opening and a cap which is hermetically secured to said opening to keep an inside of the container main body at a reduced pressure, comprises;

liquid content taking means including a suction nozzle which is insertable into the container main body through said cap;

means for rotating said container substantially up side down; and air supplying means including an air supply nozzle which is insertable into the container main body through said cap and an air supply source connected to said air supply nozzle to supply an air into said container main body.

In this apparatus according to the invention, the pressure inside the container main body is not reduced by supplying the air into the container main body while the liquid content is sucked into the suction nozzle, so that the control for the suction force becomes very simple and a given amount of the liquid content can be taken out of the container in a simple and accurate manner. Further, the container main body is rotated up side down, a tip of the suction nozzle is always immersed into the liquid content, so that the insertion depth of the tip of the suction nozzle can be controlled simply.

BRIEF DESCRIPTION OF THE DRAWINGS

FIG. 1 is a schematic view showing a known apparatus for removing the rubber cap from the container;

FIG. 2 is a schematic view illustrating the principal construction of the apparatus according to the invention for removing a cap from a container;

FIG. 3 is a schematic view depicting a first embodiment of the apparatus according to the invention for removing the cap;

FIG. 4 is a schematic view showing a second embodiment of the cap removing apparatus according to the invention;

FIG. 5 is a schematic view representing a third embodiment of the cap removing apparatus according to the invention;

FIG. 6 is a graph showing the output signal of the pressure sensor provided in the apparatus illustrated in FIG. 5;

FIG. 7 is a schematic view depicting a fourth embodiment of the cap removing apparatus according to the invention;

FIG. 8 is a schematic view showing a fifth embodiment of the apparatus according to the invention for taking out a serum sample;

FIG. 9 is a schematic view representing a sixth embodiment of the apparatus according to the invention for taking out a serum sample;

FIGS. 10A, 10B, 10C and 10D are schematic views showing the operation of the apparatus illustrated in FIG. 9;

FIGS. 11A and 11B are schematic views depicting embodiments of the apparatus according to the invention.

DESCRIPTION OF THE PREFERRED EMBODIMENTS

FIG. 2 is a schematic view illustrating a principal construction of the apparatus according to the invention for removing a cap from a container main body. A vacuum type blood collection tube 10 comprises a tube 11 serving as the container main body and a rubber cap 12 which is hermetically secured to an upper opening of the tube 11. It should be noted that after a sample blood has been taken from a patient into the tube 11, a needle has been removed from the tube. The pressure inside the tube 11 is kept at a reduced or negative pressure, so that the cap 12 could not be easily removed from the tube 11. As illustrated in FIG. 2, an air supply pipe 13 having a needle-like tip is inserted into the tube 11 through the rubber cap 12, so that the inside of the tube is communicated with the atmosphere by means of the air supply pipe 13. Therefore, the pressure inside the tube 11 is increased to the atmospheric pressure. In this case, a diameter of a conduit formed within the pipe 13 is selected such that the pressure inside the tube 11 is gradually increased. Then, a pair of cap removing arms 14 are moved inwardly to hold the rubber cap 12, and after that the removing arms are moved upward to remove the rubber cap from the opening of the tube 11.

As explained above, according to the invention, the inside of the tube 11 is communicated with the atmosphere by means of the pipe 13, so that the pressure inside the tube is increased to the atmospheric pressure. Therefore, the rubber cap 12 can be removed with a smaller force in an easy and positive manner. Since the cap removing force is very small, it is no more necessary to secure the removing arms 14 to the rubber cap 12 with the aid of the pins as in the case of the known apparatus shown in FIG. 1. Therefore, the apparatus can be applied to various caps having different shape and being made of different materials.

According to another aspect of the present invention, the air supply pipe 13 is connected to an air pump to supply an air into the tube 11. By increasing the pressure inside the tube 11, there is produced a force for pushing the cap 12 upward, so that the cap removing force can be further decreased.

In order to remove the cap at a high speed, it is necessary to introduce the air at a large supply rate, but if the air supply rate is increased excessively, the sample blood contained in the tube might spread to stain surroundings. In order to mitigate such a drawback, according to further aspect of the present invention, a means for monitoring the pressure inside the tube is provided in an air supply passage, and the air supply rate is controlled in accordance with the detected pressure such that when it is detected that the cap is initiated to be removed from the opening of the tube, the air supply rate is decreased and the air supply is stopped as soon as the cap is fully removed. By providing such an air supply control, the spread of the sample blood out of the tube upon removing the cap can be avoided and further the cap can be removed at a high speed.

FIG. 3 is a schematic view illustrating a first embodiment of the cap removing apparatus according to the invention. A vacuum type blood collection tube 20 comprises a tube 21 having an upper opening and a rubber cap 22 secured to the opening of the tube 21 in a hermetic manner to keep the inside of the tube at a negative pressure. Within the tube 21 a sample blood collected from a patient is contained. At first, the tube 21 is supported by a holder 27 in an upright position. Then, a solenoid 25 is energized to move arms 24 inwardly. Top ends of the arms 24 are bent inwardly such that the top ends can be engaged with a lower surface of a flange of the rubber cap 22. Between the arms 24 there is provided a coiled spring 26 such that the arms are biased to move inwardly. Therefore, a distance between the tips of the arms 24 can be adjusted by selectively energizing the solenoid 25, so that the apparatus can be equally applied to various caps having different sizes.

After the rubber cap 24 is supported by the top ends of the arms 24, an electric motor 29 is energized to move a pipe 23 downward by means of a rack gear 28a formed in a block 28 supporting the pipe 23 and a pinion gear 28b secured to an output shaft of the motor. During the downward movement of the pipe 23, the pipe is inserted into the rubber cap 22 such that the tip of the pipe situates at a point within a space between the cap 22 and a liquid content. When the pipe 23 is inserted into the tube 21, the inside of the tube is communicated with the surrounding atmosphere and the pressure inside the tube is increased up to the atmospheric pressure.

Then, an electric motor 31 is energized to move the arms 24 upward by means of a rack gear 30a and a pinion gear 30b. During this upward movement of the arms 24, the rubber cap 23 is lifted to be removed from the opening of the tube 21. It should be noted that in the present embodiment, the cap 23 is removed by engaging the front ends of the arms 24 with the lower surface of the flange of the cap, but it is also possible to clamp the cap by the front ends of the arms.

FIG. 4 is a schematic view showing a second embodiment of the apparatus for removing the cap from the tube according to the invention. In the present embodiment, portions similar to those of the first embodiment illustrated in FIG. 3 are denoted by the same reference numerals used in FIG. 3. In the second embodiment, the pipe 23 is connected to an air compressor 32 by means of a tube 33. After the pipe has been inserted into the tube 21 of the blood collection tube 20 through the rubber cap 22, the air compressor 32 is driven to supply the air into the tube 21 through the tube 33 and pipe 23, so that the pressure inside the tube 21 is increased up to a positive pressure. When the pressure inside the tube 21 is increased higher than the atmospheric pressure, there is produced a force for pushing the cap upward, so that the cap can be removed much more easily. The air compressor 32 may be replaced by any other air supply pump such as bellows pump or air syringe.

FIG. 5 is a schematic view depicting a third embodiment of the cap removing apparatus according to the invention. In order to remove the cap much more speedily, an air supply rate may be increased. However, if the air supply rate is increased excessively, the blood sample might be spread out of the tube when the cap 23 is removed from the opening due to the fact that a strong air flow is introduced into the tube. In the present embodiment, in order to avoid such a spread of the blood sample, in the tube 33 for connecting the pipe 23 to the air compressor 32 there is arranged a pressure sensor 35, so that the pressure inside the tube 21 is monitored. An output signal of the pressure sensor 35 is supplied to a controller 36 which controls the operation of the air compressor 32 in accordance with the monitored pressure inside the tube 21.

FIG. 6 is a graph showing the variation of the output signal of the pressure sensor 35 during the cap removing operation. When the controller 36 detects a point A at which the cap removing operation is just initiated, the air supply rate is decreased. Further, a point B at which the cap 23 has been fully removed is detected, the air supply is stopped. By controlling the air supply in accordance with the pressure inside the tube 21 in the manner explained above, it is possible to prevent the spread of the blood sample out of the tube 21 when the cap 23 is removed from the opening of the tube, so that any undesired contamination could be avoided.

FIG. 7 is a schematic view showing a fourth embodiment of the cap removing apparatus according to the invention. In the present embodiment, the condition of the cap removing operation is detected by a position sensor 37 instead of the pressure sensor. The position sensor 37 constituted by a micro-switch or photo-interruptor is arranged on a path along which the cap 23 is removed from the opening of the tube 21. Therefore, when the position sensor 37 detects the removal of the cap 23 to send a signal to the controller 36, the air supply rate is reduced. After a predetermined time period has passed, the air supply is stopped.

In the embodiments so far explained, the cap 23 is made of rubber, but the present invention may be equally applied to various caps made of different materials than rubber. For instance, the cap may be made of plastics.

As explained above, in the cap removing apparatus according to the invention, the pressure inside the tube is increased up to the atmospheric pressure or positive pressure, and thus the cap can be easily removed from the opening of the tube. During the cap removing operation, the tube is not subjected to an excessive force, it can be effectively prevented from being broken. Further, it is no more necessary to grasp the tube with a strong force or to swing the cap removing arms, and therefore the apparatus can be made very simple and less expensive.

In the embodiments in which the air is supplied to the tube to increase the pressure inside the tube higher than the atmospheric pressure, the cap can be remove very quickly and the processing ability is increased. Moreover, in such embodiments, the removing arms are sufficient to serve as members for merely holding the removed cap, so that apparatus can be utilized for various kinds of caps. Further, when the air supply rate is controlled in accordance with the condition of the cap removing operation, it is possible to prevent the liquid content from being spread out of the tube when the cap is removed, and thus undesired contamination can be effectively avoided.

The present invention also provides the apparatus for taking a liquid content from a hermetically sealed container by piercing a suction nozzle having a needle tip through a cap of the container. For instance, it is sometimes required to taking a serum of a blood sample contained in the vacuum type blood collection tube. In this case, after the serum and clot of the sample blood have been separated in the tube with the aid of the centrifugal device, the suction nozzle is inserted into the tube through the cap and the serum is sucked into the suction nozzle.

FIG. 8 is a schematic view showing a fifth embodiment of the apparatus according to the invention for taking the liquid content by means of the suction nozzle. A sample blood has been collected in a vacuum type blood collection tube 50 including a tube 51 having an opening and a rubber cap 53 hermetically secured to the opening of the tube 52 to keep the inside of the tube at a negative pressure. Further the sample blood has been separated into a serum S and a clot C by means of a centrifugal device. A suction nozzle 53 and an air supply nozzle 54 are secured to a supporting member 55 which is moved up and down by means of an electric motor 56, pinion gear 57a secured to an output shaft of the motor and a rack gear 57b provided on a side wall of the supporting member. The suction nozzle 53 is arranged such that it is movable up and down with respect to the supporting member 55. That is to say, the suction nozzle 53 is moved up and down by means of an electric motor 58, a pinion gear 59a secured to an output shaft of the motor 58, and a rack gear 59b secured to the suction nozzle. The suction nozzle 53 is connected to a syringe 60 by means of a tube 61 and a piston rod 60a of the syringe is driven by means of an electric motor 62, a pinion gear 63a and a rack gear 63b. Further the air supply nozzle 54 is coupled with an air compressor 64 by means of a tube 65.

Now the operation of the apparatus shown in FIG. 8 will be explained. At first, the motor 58 is driven such that a tip of the suction nozzle 53 is protruded from the supporting member 55 to a substantially same level as a tip of the air supply nozzle 54. Then, the motor 56 is energized in one direction to move the supporting member 55 downward, so that the suction nozzle 53 and air supply nozzle 54 are inserted into the tube through the rubber cap 52. In this case, the tips of these nozzles 53 and 54 situate within a space between the serum S and the rubber cap 52. Next the motor 58 is driven to move the suction nozzle downward such that the tip of the suction nozzle is immersed into the serum S. In this case, it is preferable to move the tip of the suction nozzle 53 downward just above a boundary layer B between the serum S and the clot C, the boundary layer being essentially formed by a separating agent. In order to move the suction nozzle 53 into such a position, in the present embodiment there is arranged a sensor 65 for optically detecting the boundary layer B. An output signal of the sensor 65 is supplied to a driving circuit of the motor 58. Then, the air compressor 64 is energized to supply the air into the tube 51 through the tube 65 and air supply nozzle 55 to increase the pressure inside the tube. At the same time, the motor 62 is energized to drive the piston rod 60a of the syringe 60 to suck the serum S into the suction nozzle 53. While the serum is sucked into the suction nozzle 53, the air is supplied into the tube 51, and therefore the pressure inside the tube is not reduced. In this manner, the serum S contained in the vacuum type blood collection tube 50 can be taken out effectively.

FIG. 9 is a schematic view showing a sixth embodiment of the apparatus according to the invention. In the embodiment illustrated in FIG. 8, the boundary layer B between the serum S and the clot C is optically detected by the sensor. However, in some cases it would be difficult to detect the boundary layer B reliably due to the label applied on the outer surface of the blood collection tube. In the present embodiment, a given amount of the serum can be taken out of the tube without detecting the boundary layer B. In the present embodiment, portions similar to those shown in FIG. 8 are denoted by the same reference numerals used in FIG. 8. In the blood collection tube 50 comprising the tube 51 and rubber cap 52, the serum S and the clot C are separated by the boundary layer B. The apparatus comprises a block 71 which is arranged movably up and down as well as rotatably about a shaft 72. To the block 71 are secured a pair of arms 73 for holding the tube 51. Further the suction nozzle 53 and air supply nozzle 54 both made of stainless steal are secured to the block 71. To one side wall of the block 71 there is secured a rack gear 57b which is engaged with a pinion gear 57a secured to an output shaft of an electric motor 56. By energizing the motor 56, the block 71 is moved up and down together with the suction nozzle 53 and air supply nozzle 54.

In the other side wall of the block 71 there is formed a semicircular rack gear 74 which is engaged with a pinion gear 75 which is connected to an output shaft of an electric motor 76. By driving the motor 76, the block 71 is rotated about the shaft 72. The suction nozzle 53 is coupled with a syringe 60 by means of joint 77 and tube 61 made of polytetrafluoroethylene. To the tube 61 is also connected a pressure sensor 78. The air supply nozzle 54 is coupled with an air compressor 64 by means of joint 79, tube 65 made of polytetrafluoroethylene, air supply rate adjustor 80 and decompression valve 81.

Now the operation of the apparatus shown in FIG. 9 will be explained also with reference to FIG. 10. At first, the rubber cap 52 of the vacuum type blood collection tube 50 is removed and a separating agent mainly consisting of silicon is added to the sample blood contained in the tube 51. Then, after the rubber cap 52 has been inserted into the opening of the tube 51, the tube is set in a centrifugal device to separate the serum S and the clot C by the boundary layer B. Next, the blood collection tube 50 is held by the arms 73 as depicted in FIG. 10A, and then the motor 56 is energized to move the block 71 downward. During this downward movement of the block 71, the tips of the suction nozzle 53 and air supply nozzles 54 are pierced through the rubber cap 52 and are inserted into the tube 51 as shown in FIG. 10B. Next, the motor 76 is driven to rotate the block 71 by means of the pinion gear 75 and semicircular rack gear 74 to move the tube 50 into a substantially up-side-down position. During this rotational movement, only the serum S is moved downward, because the clot C are remained in the bottom portion of the tube 51 by means of the boundary layer B. After that, the syringe 60 is operated to suck a given amount of the serum S into the suction nozzle 53 as depicted in FIG. 10D. At the same time, the air compressor 64 is energized to supply the air into the tube 51 by means of the air supply nozzle 54. Usually the inside of the tube 51 is kept at a negative pressure, and in such a case the air is introduced into the tube 51 such that the original negative pressure and a negative pressure produced by sucking the serum have to be compensated for. The pressure of the air supplied into the tube 51 is controlled by the decompression valve 80 and the air supply rate is controlled by the air supply rate adjuster 81 such that an amount of the air supplied into the tube is substantially same as an amount of the serum S sucked into the suction nozzle 53. The suction of the serum S into the suction nozzle 53 is controlled by monitoring the pressure inside the tube 51 by the sensor 78. When it is detected that the tip of the suction nozzle 53 is going to extend above a level of the serum S, the suction is stopped so that an air is not introduced into the suction nozzle.

After a given amount of the serum S has been sucked into the suction nozzle 53, the motor 76 is driven in the opposite direction to rotate the block 71 into the initial position. Then, the motor 56 is driven again in the opposite direction to move the block 71 upward to remove the suction nozzle 53 and air supply nozzle 54 from the tube 50. The serum sucked into the suction nozzle 53 is discharged from the tip of the suction nozzle into a suitable reaction vessel by moving the piston rod 60a in the opposite direction.

In the above explained embodiment shown in FIG. 9, the tips of the suction nozzle 53 and air supply nozzle 54 are inserted into the tube 51 up to the substantially same level as illustrated in FIG. 11A. Therefore, the tip of the air supply nozzle 54 is in the serum S and the air is introduced into the tube 51 in the form of air bubbles. Then, the air bubbles might be sucked into the auction nozzle 53, and therefore an amount of the serum sucked into the suction nozzle becomes smaller than a desired amount. In order to avoid such a drawback, according to the invention the tip of the air supply nozzle 54 may be deeply inserted into the tube 51 such that the tip of the nozzle protrudes above a level of the serum S as shown in FIG. 11B.

As explained above, according to the present invention, a precisely controlled amount of the liquid content can be taken out of the hermetically sealed container without being affected by the variation of the pressure inside the container. Further, in the embodiment illustrated in FIG. 9, a predetermined amount of the serum can be always taken out of the vacuum type blood collection tube without detecting the position of the boundary layer between the serum and the blood cells. Moreover, since it is not necessary to insert the suction nozzle deeply into the tube, undesired contamination between successive samples can be effectively reduced.

What is claimed is:

1. An apparatus for taking a liquid content for use in analysis out of a container, the container including a container main body having an opening and a cap which is hermetically secured to the opening to keep an inside of the container main body at an initial pressure, the apparatus comprising:

liquid content taking means for taking at least part of the liquid content out of the container via the opening, the liquid content taking means comprising means for removing the cap from the opening of the container main body; and air supplying means for supplying air into the container main body through the cap;

the air supplying means including an air supply nozzle having a proximal end which is insertable into the container main body through the cap, an air supply source connected to a distal end of the air supply nozzle, means for detecting a pressure inside the container main body, and means for controlling operation of the air supply source in accordance with the pressure detected inside the container main body, said air supplying means operating such that the pressure inside the container main body is increased to a pressure above the atmospheric pressure;

said air supplying means controlling the pressure inside the container main body by supplying the air into the container main body while the liquid content taking means operates on the container.

2. An apparatus according to claim 1, wherein the air supplying means operates such that the pressure inside the container main body is kept substantially at the atmospheric pressure.

3. An apparatus according to claim 1, wherein said means for removing the cap from the opening of the container main body comprises means for holding the container main body, a pair of arms which are engageable with the cap, means for moving said pair of arms inwardly and outwardly, and means for moving said pair of arms up and down.

4. An apparatus according to claim 1, wherein the liquid content taking means comprises a suction nozzle that is inserted into the container main body via the cap.

5. An apparatus according to claim 1, wherein the proximal end of the air supply nozzle comprises a hollow needle.

* * * * *